US010584375B2

(12) United States Patent
Dambacher et al.

(10) Patent No.: US 10,584,375 B2
(45) Date of Patent: *Mar. 10, 2020

(54) GENOTYPING BY POLYMERASE BINDING

(71) Applicant: Omniome, Inc., San Diego, CA (US)

(72) Inventors: Corey M. Dambacher, La Jolla, CA (US); Michael Van Nguyen, San Diego, CA (US)

(73) Assignee: OMNIOME, INC., San Diego, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 15/900,308

(22) Filed: Feb. 20, 2018

(65) Prior Publication Data

US 2018/0208980 A1 Jul. 26, 2018

Related U.S. Application Data

(63) Continuation of application No. 15/701,373, filed on Sep. 11, 2017, now Pat. No. 9,932,631.

(60) Provisional application No. 62/448,630, filed on Jan. 20, 2017.

(51) Int. Cl.
| | | |
|---|---|---|
| C12Q 1/68 | (2018.01) | |
| C12Q 1/6853 | (2018.01) | |
| C12Q 1/686 | (2018.01) | |
| C12Q 1/6872 | (2018.01) | |
| C12Q 1/6883 | (2018.01) | |
| C12Q 1/6886 | (2018.01) | |
| C12Q 1/6827 | (2018.01) | |

(52) U.S. Cl.
CPC .......... *C12Q 1/6853* (2013.01); *C12Q 1/686* (2013.01); *C12Q 1/6827* (2013.01); *C12Q 1/6872* (2013.01); *C12Q 1/6883* (2013.01); *C12Q 1/6886* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,679,524 A | 10/1997 | Nikiforov et al. | |
| 6,004,744 A | 12/1999 | Goelet et al. | |
| 6,013,431 A | 1/2000 | Soderlund et al. | |
| 6,150,095 A | 11/2000 | Southern et al. | |
| 6,153,379 A | 11/2000 | Caskey et al. | |
| 6,280,954 B1 | 8/2001 | Ulfendahl | |
| 6,355,431 B1 | 3/2002 | Chee et al. | |
| 6,537,748 B1 | 3/2003 | Goelet et al. | |
| 6,908,736 B1 | 6/2005 | Densham | |
| 7,008,766 B1 | 3/2006 | Densham | |
| 7,264,934 B2 | 9/2007 | Fuller | |
| 7,476,503 B2 | 1/2009 | Turner et al. | |
| 7,604,963 B2 | 10/2009 | Densham | |
| 7,888,073 B2 | 2/2011 | Densham | |
| 8,133,672 B2 | 3/2012 | Bjornson et al. | |
| 8,399,196 B2 | 3/2013 | Hoser | |
| 8,632,975 B2 | 1/2014 | Vander Horn et al. | |
| 8,652,781 B2 | 2/2014 | Korlach | |
| 8,679,747 B2 * | 3/2014 | Olasagasti ........... | C12Q 1/6869 435/6.1 |
| 9,045,796 B2 | 6/2015 | Gunderson et al. | |
| 9,279,154 B2 | 3/2016 | Previte et al. | |
| 9,279,155 B2 | 3/2016 | Bjornson et al. | |
| 9,353,412 B2 | 5/2016 | He et al. | |
| 9,556,480 B2 | 1/2017 | Turner et al. | |
| 9,695,471 B2 | 7/2017 | Beechem et al. | |
| 9,719,073 B2 | 8/2017 | Emig et al. | |
| 9,932,631 B1 | 4/2018 | Dambacher et al. | |
| 10,113,197 B2 | 10/2018 | Sun et al. | |
| 10,415,029 B2 | 9/2019 | Dambacher et al. | |
| 2006/0051807 A1 | 3/2006 | Fuller | |
| 2010/0330570 A1 | 12/2010 | Vander Horn et al. | |
| 2016/0032379 A1 | 2/2016 | Gloeckner et al. | |
| 2017/0022553 A1 | 1/2017 | Vijayan et al. | |

FOREIGN PATENT DOCUMENTS

| | | |
|---|---|---|
| WO | 2005019476 | 3/2005 |
| WO | 2007091077 | 8/2007 |
| WO | 2010141390 | 12/2010 |

OTHER PUBLICATIONS

U.S. Appl. No. 15/701,358, "Notice of Allowance", dated Jul. 30, 2019, 10 pages.
PCT/US2017/051023, "International Preliminary Report on Patentability", dated Aug. 1, 2019, 7 pages.
PCT/US2017/051025, "International Preliminary Report on Patentability", dated Aug. 1, 2019, 7 pages.
Datta et al., "Salt Dependence of DNA binding by Thermus aquaticus and *Escherichia coli* DNA Polymerases", Journal of Biological Chemistry, vol. 278, Issue of Feb. 21, 2003: 5694-5701.
Deredge et al., "The Glutamate Effect on DNA Binding by Pol I DNA Polymerases: Osmotic Stress and the Effective Reversal of Salt Linkage", J. Mol. Biol., vol. 401, 2010, 223-238.
Klenow et al., "Effect of Monovalent Cations on the Activity of the DNA Polymerase of *Escherichia coli* B", European J. Biochem., 1696, 133-141.
Nikiforov et al., "Genetic Bit Analysis: a solid phase method for typing single nucleotide polymorphisms", Nucl. Acids Res., vol. 22, No. 20, 1994, pp. 4167-4175.
Pastinen et al., "A System for Specific, High-throughput Genotyping by Allele-specific Primer Extension on Microarrays", Genome Research, Cold Spring Harbor Laboratory Press, vol. 10, 2000, 1031-1042.

(Continued)

*Primary Examiner* — James Martinell
(74) *Attorney, Agent, or Firm* — Kilpatrick Townsend & Stockton LLP

(57) ABSTRACT

A method for identifying target alleles, that includes steps of (a) forming a plurality of stabilized ternary complexes at a plurality of features on an array, wherein the stabilized ternary complexes each has a polymerase, a template nucleic acid having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (b) detecting stabilized ternary complexes at the features, thereby identifying the target alleles.

18 Claims, 5 Drawing Sheets

(56) References Cited

OTHER PUBLICATIONS

Pastinen et al., "Minisequencing: A Specific Tool for DNA Analysis and Diagnostics on Oligonucleotide Arrays", Genome Research, Cold Spring Harbor Laboratory, vol. 7, 1997, 606-614.

Richard, A. J. et al., "Thermal stability landscape for Klenow DNA polymerase as a function of pH and salt concentration," Biochemica et Biophysica Acta, 2006, vol. 1764, pp. 1546-1552.

Syvanen et al., "A Primer-Guided Nucleotide Incorporation Assay in the Genotyping of Apolipoprotein E", Genomics, 1990, 8(4):684-692.

Syvanen, "Accessing Genetic Variation: Genotyping Single Nucleotide Polymorphisms", Nature Reviews: Genetics, 2, 2001, 930-942.

Syvanen et al., "Detection of Point Mutations by Solid-Phase Methods", Human Mutation 3, 1994, 172-179.

Chen et al., "The History and Advances of Reversible Terminators Used in New Generations of Sequencing Technology", Genomics Proteomics Bioinformatics, 11(1), Feb. 1, 2013, pp. 34-40.

Roettger et al., "Mismatched and Matched dNTP Incorporation by DNA Polymerase β Proceed via Analogues Kinetic Pathways", Biochemistry, 47, Sep. 16, 2008, pp. 9718-9727.

Tsai et al., "Site-specific labeling of T7 DNA polymerase with a conformationally sensitive flurophore and its use in detecting single-nucleotide polymorphisms", Analytical Biochemistry, vol. 384, No. 1, Academic Press Inc., New York, Jan. 1, 2009, pp. 136-144.

PCT/US2017/051025, "International Search Report and Written Opinion", dated Nov. 9, 2017, 12 pages.

U.S. Appl. No. 15/701,373, "Notice of Allowance", dated Feb. 1, 2018, 8 pages.

Fuller et al., "The challenges of sequencing by synthesis", Nature Biotechnology, vol. 27, No. 11, Nov. 2009, pp. 1013-1023.

PCT/US2017/051023, "International Search Report and Written Opinion", dated Nov. 29, 2017, 14 pages.

Previte et al., "DNA sequencing using polymerase substrate-binding kinetics", Nature Communications, Nature Publishing Group, United Kingdom, vol. 6, Jan. 23, 2015, 12 pages.

CA3,050,852, "Office Action", dated Aug. 27, 2019, 5 pages.

AU2017394645, "Examination Report", dated Sep. 27, 2019, 3 pages.

\* cited by examiner

GENOTYPING BY POLYMERASE BINDING

CROSS-REFERENCE TO RELATED APPLICATION

This application is a continuation of U.S. application Ser. No. 15/701,373, filed Sep. 11, 2017, which claims the benefit of U.S. Provisional Application No. 62/448,630, filed Jan. 20, 2017, the contents of which are hereby incorporated by reference in their entirety.

BACKGROUND

Small differences in nucleic acid sequences can result in significant differences in biological function. For example, single nucleotide polymorphisms (SNPs) in the human genome underlie differences in susceptibility to disease. A wide range of human diseases, such as sickle-cell anemia, β-thalassemia, Alzheimer's Disease and cystic fibrosis result from SNPs. Recent advances in genotyping and DNA sequencing have identified a large number of SNPs that are associated with the probability of developing a variety of diseases and conditions. Such SNPs can be useful for diagnosis and prognosis of the disease or conditions to which they have been associated. Furthermore, many of these SNPs are likely to be therapeutically relevant genetic variants and/or involved in genetic predisposition to disease. However, accurate diagnostic correlations generally require evaluation of large SNP panels (e.g. on a genome-wide scale) for a large population of individuals. Currently available methods are costly and time consuming which is unfavorable for scaling the methods to clinically meaningful levels.

Thus, there exists a need for efficient methods to detect a large variety of SNPs, or other nucleic acid polymorphisms, often in many individuals. The present disclosure satisfies this need and provides related advantages as well.

BRIEF SUMMARY

The present disclosure provides a method for identifying target alleles in a mixture of nucleic acids. The method can include steps of (a) forming a plurality of stabilized ternary complexes at a plurality of features on an array, wherein the stabilized ternary complexes each has a polymerase, a template nucleic acid having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (b) detecting stabilized ternary complexes at the features, thereby identifying the target alleles.

In some embodiments, the method for identifying target alleles in a mixture of nucleic acids can include steps of (a) providing an array of features, wherein different locus-specific primers are attached at different features of the array; (b) contacting the array with a plurality of nucleic acid templates, polymerases and nucleotides to form a plurality of stabilized ternary complexes at a plurality of the features, wherein the stabilized ternary complexes each has a polymerase, template nucleic acid having a target allele of a locus, a locus-specific primer hybridized to the locus, and a next correct nucleotide that is a cognate to the target allele; and (c) detecting stabilized ternary complexes at the features, thereby identifying the target alleles.

An alternative embodiment of the method for identifying target alleles in a mixture of nucleic acids can include steps of (a) providing an array of features, wherein different allele-specific primers are attached at different features of the array; (b) contacting the array with a plurality of nucleic acid templates, polymerases and nucleotides to form a plurality of stabilized ternary complexes at a plurality of the features, wherein the stabilized ternary complexes each has a polymerase, template nucleic acid having a target allele of a locus, an allele-specific primer hybridized to the locus, and a next correct nucleotide having a cognate in the locus, wherein the 3' end of the allele-specific primer has a cognate nucleotide for the target allele; and (c) detecting stabilized ternary complexes at the features, thereby identifying the target alleles.

This disclosure further provides, a method for identifying target alleles in a mixture of nucleic acids that includes steps of (a) providing an array of features, wherein different locus-specific primers are attached at a first subset of the features of the array, and wherein different allele-specific primers are attached at a second subset of the features of the array; (b) contacting the array with a plurality of nucleic acid templates, polymerases and nucleotides to form a plurality of stabilized ternary complexes at a plurality of the features, wherein the stabilized ternary complexes at the first subset of features each has a polymerase, template nucleic acid having a target allele of a locus, a locus-specific primer hybridized to the locus, and a next correct nucleotide that is a cognate to the target allele, wherein the stabilized ternary complexes at the second subset of features each has a polymerase, template nucleic acid having a target allele of a locus, an allele-specific primer hybridized to the locus, and a next correct nucleotide having a cognate in the locus, and wherein the 3' end of the allele-specific primer has a cognate nucleotide for the target allele; and (c) detecting stabilized ternary complexes at the features, thereby identifying the target alleles.

Also provided is a method for identifying target alleles in a mixture of nucleic acids, that includes steps of (a) providing an array of features, wherein different template nucleic acids are attached at different features of the array; (b) contacting the array with a plurality of primers, polymerases and nucleotides to form a plurality of stabilized ternary complexes at a plurality of the features, wherein the stabilized ternary complexes at the features each has a polymerase, a template nucleic acid attached to a feature of the array and having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (c) detecting stabilized ternary complexes at the features, thereby identifying the target alleles.

Further provided is a method for identifying target alleles in a mixture of nucleic acids that includes steps of (a) providing an array of features, wherein polymerases are attached at features of the array; (b) contacting the array with a plurality of primers, template nucleic acids and nucleotides to form a plurality of stabilized ternary complexes at a plurality of the features, wherein the stabilized ternary complexes at the features each has a polymerase that is attached at a feature of the array, template nucleic acid having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (c) detecting stabilized ternary complexes at the features, thereby identifying the target alleles.

DETAILED DESCRIPTION

The present disclosure provides polymerase-based methods for detecting or identifying target alleles of interest. Embodiments of the methods exploit the specificity with which a polymerase can form a stabilized ternary complex with a primed template and a next correct nucleotide. For example, a stabilized ternary complex can be formed between a polymerase, primed template having a target allele and cognate nucleotide for the allele. An advantage of the methods is that polymerase specificity allows a target allele to be distinguished from other nucleic acids, including for example, other alleles that differ from the target allele, in some cases by only a single nucleotide. For example, a ternary complex can be formed between a polymerase, a primed template encoding a target single nucleotide polymorphism (SNP) allele and a cognate nucleotide for the SNP allele. Detection of the ternary complex will result in selective detection of the SNP allele, compared to a non-target SNP allele at the same locus, because the cognate nucleotide is selective for the target SNP when forming a ternary complex with the polymerase.

Figure 1A:
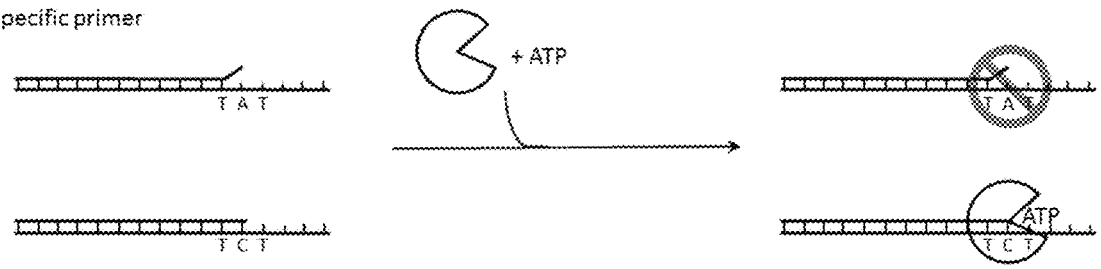
FIG. 1A is a schematic showing a diagrammatic representation for allele-specific ternary complex formation using a polymerase (represented as a pie shape), allele-specific primer bound to a template, and cognate nucleotide that binds at a position on the template that is adjacent to the allele position.

Methods and compositions set forth herein can be used to detect rare alleles (e.g. DNA- or RNA-based) containing various mutations within their sequences. The methods are well suited to detect even rare variant alleles from pools of purified or semi-purified oligonucleotides containing wild-type DNA sequences of the same locus, as well as other unrelated sequences. FIG. 1 shows diagrammatic representations for two different primer-nucleotide combinations that can be used to form allele-specific ternary complexes. As shown in FIG. 1A an allele-specific primer can be used such that the 3' end of the primer is selectively matched to a target allele at a specific locus, but mismatched to other alleles at the locus. For example, in the case of a single nucleotide polymorphism (SNP) locus the 3' end of the primer base-pairs with the targeted SNP allele C at position N of the locus, but not with allele A at position N of the locus. Upon addition of a polymerase and next correct nucleotide for position N+1 of the locus (i.e. ATP in the Figure) a stabilized ternary complex can be formed selectively for the target allele, under conditions that do not form stabilized ternary complex with the mismatched, non-target allele.

Figure 1B:
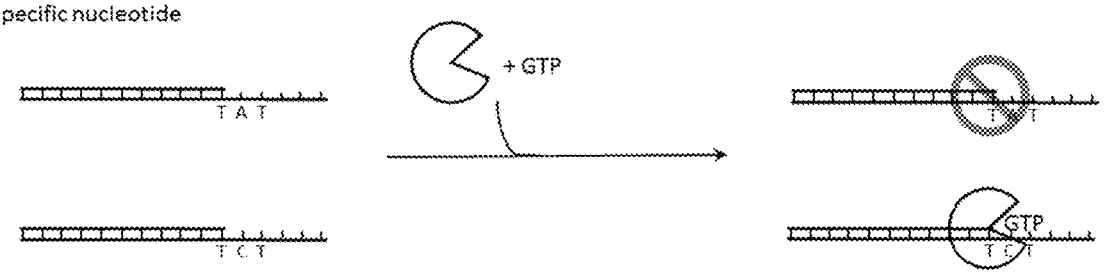
FIG. 1B is a schematic showing a diagrammatic representation for allele-specific ternary complex formation using a polymerase (represented as a pie shape), allele-specific cognate nucleotide and a locus primer that binds at a region adjacent to the allele position.

Alternatively, as shown in FIG. 1B, a locus-specific primer can be used that binds to multiple alleles of a particular locus, such that the 3' end of the locus primer base-pairs with N−1 position of the locus. This configuration leaves the target allele of interest (at position N) available for binding to an allele-specific cognate nucleotide. Again, taking the example of a SNP locus, the primer hybridizes to both alleles. Upon addition of a polymerase and the cognate nucleotide for the target SNP (i.e. the target SNP being C and the cognate nucleotide being GTP in the Figure), a stabilized ternary complex can be formed selectively for the target allele, under conditions that do not form stabilized ternary complex with the non-target, A allele.

Figure 2:
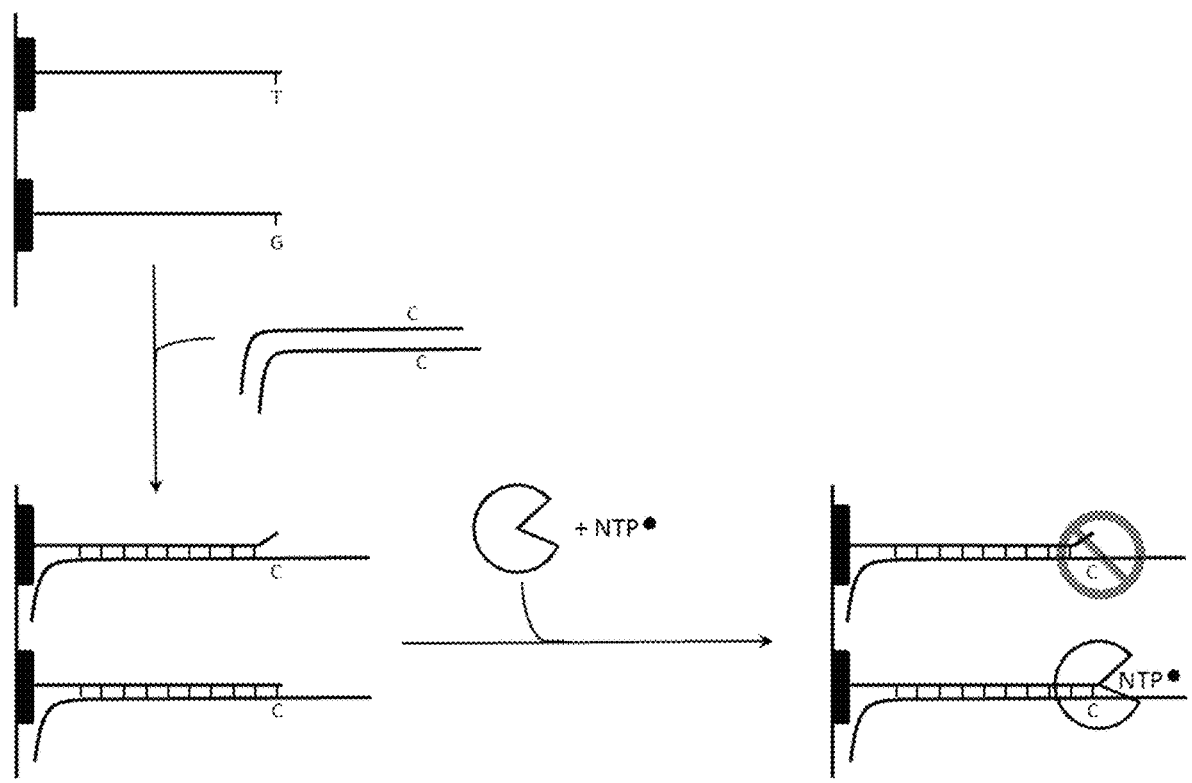
FIG. 2 is a schematic showing a diagram of a detection method that distinguishes alleles spatially according to the location of signals arising from labels that are bound in stabilized-ternary complexes to allele-specific primers at different features of an array.

An exemplary detection mode using allele-specific primers is shown in FIG. 2. A first allele-specific primer is present at a first feature of an array and a second allele-specific primer is present at a second feature of the array. The primer at the top feature has a 3' T that is complementary to the A allele and the primer at the bottom feature has a G that is complementary to the C allele. In the first step, a mixture of nucleic acid templates is hybridized to the array. For purposes of illustration, only the C allele is present in the mixture shown in the figure. At the top feature a mismatch results whereas a perfect match results at the bottom feature. The array is then contacted with polymerases and a mixture of four different nucleotide types all having the same label (NTP having a label indicated by a closed circle in the figure). The mismatch at the top feature inhibits polymerase binding, whereas the matched hybrid at the bottom feature can bind polymerase and a next correct nucleotide to form a stabilized ternary complex. Optionally the array can be washed, in the presence of the labeled nucleotides, to further remove contaminants from the features. The array can then be detected using a device that spatially resolves the features and senses the presence or absence of the labels. In this case, detection would show that the C allele is present (i.e. since signal is detected at the lower feature) and the A allele is absent (i.e. since no signal is detected at the top feature). The configuration in FIG. 2 is an example, where different loci and different alleles of respective loci can be distinguished due to spatial location on the array.

Figure 3:
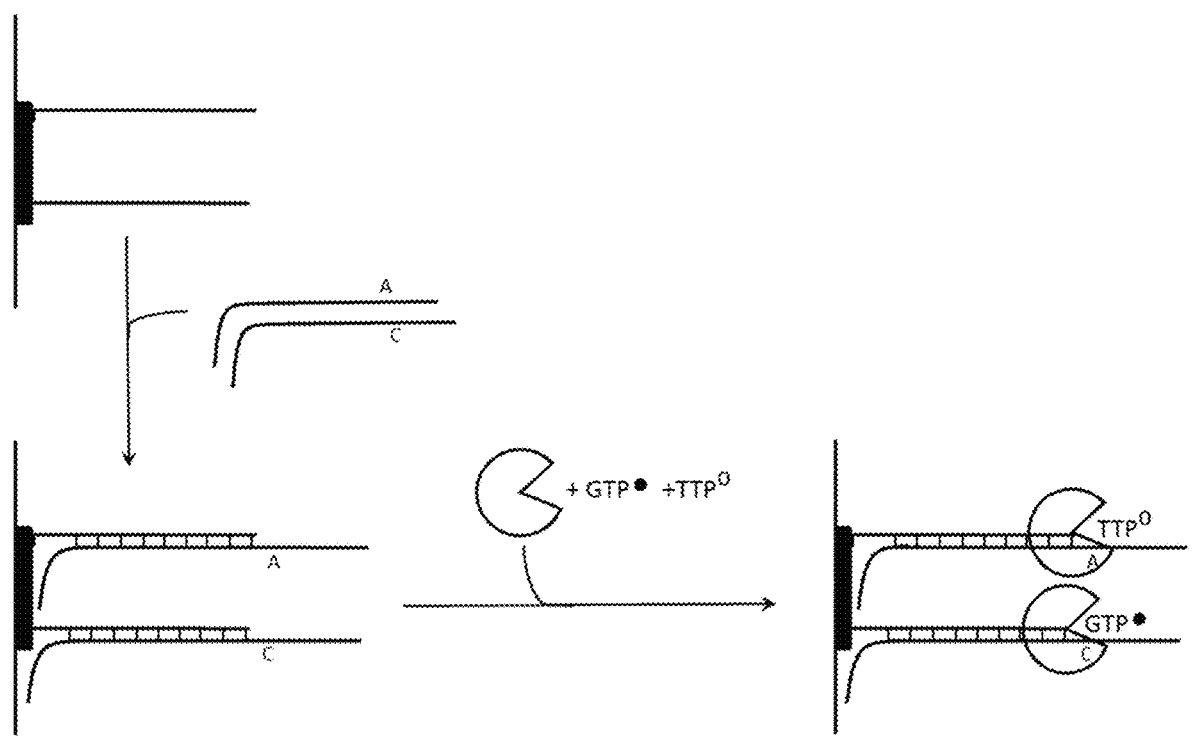
FIG. 3 is a schematic showing a diagram of a detection method that distinguishes alleles of a locus based on differentially labeled nucleotides that are bound in stabilized-ternary complexes to locus-specific primers that are present within a single feature of an array.

FIG. 3 shows a diagrammatic representation for a detection method that utilizes locus-specific primers and allele-specific cognate nucleotides that are distinguishably labelled. In the first step, nucleic acid templates having different alleles are hybridized to a feature on an array having multiple copies of the locus-specific primer. In the example shown, two different alleles bind at the feature. Polymerases are then bound to the primer-template hybrids in the presence of two different nucleotide types having distinct labels (GTP having a first label indicated by a closed circle and TTP having a second label indicated by an open circle in the figure) to form stabilized ternary complexes.

Optionally the array can be washed, in the presence of the labeled nucleotides, to further remove contaminants from the features. The array can then be detected using a device that distinguishes the two labels. In this case, detection would show that both alleles are present at the feature. The configuration in FIG. 3 is an example, where different loci can be distinguished due to spatial location on the array and alleles can be distinguished due to differential labelling of allele-specific cognate nucleotides at each feature.

Terms used herein will be understood to take on their ordinary meaning in the relevant art unless specified otherwise. Several terms used herein and their meanings are set forth below.

As used herein, the term "allele," when used in reference to a genetic locus, refers to any of the alternative nucleotides, sequences or other genetic features that occur at the genetic locus. Exemplary alleles include, but are not limited to single nucleotide polymorphisms (SNPs), insertions and/or deletions (indels), alternative mRNA splice sites or repeats that occur at a locus.

As used herein, the term "allele-specific primer" refers to an oligonucleotide that is complementary to one allele of a locus and not to another allele of the locus. A portion of an allele-specific primer can be complementary to both alleles, so long as at least one nucleotide in the primer is a cognate for only one of the alleles. For example, an allele-specific primer can have a 3' nucleotide that is a cognate of a first allele at a locus, but not a cognate of a second allele at the locus. It will be understood that an allele-specific primer can have a portion, for example, a tag or linker, that lacks complementarity to either allele.

As used herein, the term "array" refers to a population of molecules that are attached to one or more solid-phase substrates such that the molecules at one feature can be distinguished from molecules at other features. An array can include different molecules that are each located at different addressable features on a solid-phase substrate. Alternatively, an array can include separate solid-phase substrates each functioning as a feature that bears a different molecule, wherein the different probe molecules can be identified according to the locations of the solid-phase substrates on a surface to which the solid-phase substrates are attached, or according to the locations of the solid-phase substrates in a liquid such as a fluid stream. The molecules of the array can be nucleotides, nucleic acid primers, nucleic acid probes, nucleic acid templates or nucleic acid enzymes such as polymerases, ligases or exonucleases.

As used herein, the term "binary complex" refers to an intermolecular association between a polymerase and a primed template nucleic acid, exclusive of a nucleotide molecule such as a next correct nucleotide of the primed template nucleic acid.

As used herein, the term "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at concentrations that stabilize formation of a complex between a polymerase, nucleotide, and primed template nucleic acid, referred to as non-catalytic concentrations of a metal ion insofar as phosphodiester bond formation does not occur. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, the term "comprising" is intended to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extension," when used in reference to a nucleic acid, refers to a process of adding at least one nucleotide to the 3' end of the nucleic acid. A nucleotide that is added to a nucleic acid by extension is said to be incorporated into the nucleic acid. Accordingly, the term "incorporating" can be used to refer to the process of joining a nucleotide to the 3' end of a nucleic acid by formation of a phosphodiester bond.

As used herein, the term "feature" means a location in an array where a particular molecule is present. A feature can contain only a single molecule or it can contain a population of several molecules of the same species. Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 micron, 50 micron, 10 micron, 5 micron, 1 micron, or 0.5 micron. Alternatively or additionally, an array can have features that are separated by greater than 0.5 micron, 1 micron, 5 micron, 10 micron, 50 micron or 100 micron. The features can each have an area of less than 1 square millimeter, 500 square micron, 100 square micron, 25 square micron, 1 square micron or less.

As used herein, the term "gel material" is intended to mean a semi-rigid material that is permeable to liquids and gases. Typically, gel material can swell when liquid is taken up and can contract when liquid is removed by drying. Exemplary gels include, but are not limited to those having a colloidal structure, such as agarose; polymer mesh structure, such as gelatin; or cross-linked polymer structure, such as polyacrylamide. Useful gels are described, for example, in U.S. Pub. No. 2011/0059865, and U.S. Pat. No. 9,012,022, each of which is incorporated herein by reference.

The term "locus," when used in reference to a nucleic acid, refers to the position in the nucleic acid where a nucleotide, nucleic acid sequence, indel, or other genetic feature occurs.

As used herein, the term "locus-specific primer" refers to an oligonucleotide that is complementary to a first locus in a nucleic acid and not to a second locus in the nucleic acid, wherein at least two alleles of the first locus are complementarity to the oligonucleotide. For example, the locus-specific primer can be complementary to a portion of the locus that is near or adjacent to the position of the two alleles in the nucleic acid. In the latter configuration, a locus-specific primer can hybridize to the nucleic acid adjacent to a next template nucleotide that is an allele. It will be understood that a locus-specific primer can have a portion, for example, a tag portion or linker, that lacks complementarity to either locus.

As used herein, the term "next correct nucleotide" refers to the nucleotide type that will bind and/or incorporate at the 3' end of a primer to complement a base in a template strand to which the primer is hybridized. The base in the template strand is referred to as the "next template nucleotide" and is immediately 5' of the base in the template that is hybridized to the 3' end of the primer. The next correct nucleotide can be referred to as the "cognate" of the next template nucleotide and vice versa. Cognate nucleotides that interact with each other in a ternary complex or in a double stranded nucleic acid are said to "pair" with each other. A nucleotide having a base that is not complementary to the next template base is referred to as an "incorrect", "mismatch" or "non-cognate" nucleotide.

As used herein, the term "non-catalytic metal ion" refers to a metal ion that, when in the presence of a polymerase enzyme, does not facilitate phosphodiester bond formation needed for chemical incorporation of a nucleotide into a primer. A non-catalytic metal ion may interact with a polymerase, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or analogs thereof such as dideoxyribonucleotide triphosphates (ddNTPs) or reversibly terminated nucleotide triphosphates (rtNTPs). Other nucleotides include nucleotide monophosphates (NMPs), and analogs thereof.

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' OH group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents incorporation of the nucleotide component of the ternary complex into the primed nucleic acid component of the ternary complex.

As used herein, the term "tiled," when used in reference to an array, refers to an array of primers that are complementary to a contiguous region of a target nucleic acid, wherein the majority of the contiguous sequence is complementary (or identical) to primer sequences in the array. The majority of a contiguous sequence that is complementary to primer sequences can be, for example, at least 60%, 75%, 80%, 90%, 95%, 98%, 99% or more of the contiguous sequence. The primers that are present in a tiled array can align with the contiguous sequence such that small gaps occur between nearest neighbor primers in the alignment and/or such that nearest neighbor primers in the alignment overlap. Nearest neighbor primer sequences that are adjacent in an alignment to the contiguous sequence can have an average gap of at most 100 nucleotides, 50 nucleotides, 25 nucleotides, 10 nucleotides, 8 nucleotides, 6 nucleotides, 5 nucleotides, 4 nucleotides, 3 nucleotides, 2 nucleotides, or 1 nucleotide. Alternatively or additionally, nearest neighbor primer sequences that overlap in an alignment to the contiguous sequence can have an average overlap of at least 1 nucleotide, 2 nucleotides, 3 nucleotides, 4 nucleotides, 5 nucleotides, 6 nucleotides, 8 nucleotides, 10 nucleotides or more. Primers that are at adjacent features of a tiled array can have sequences that are nearest neighbor primer sequences in an alignment with the contiguous region.

The embodiments set forth below and recited in the claims can be understood in view of the above definitions.

The present disclosure provides a method for identifying target alleles in a mixture of nucleic acids. The method can include steps of (a) providing an array of features, wherein different locus-specific primers are attached at different features of the array; (b) contacting the array with a plurality of nucleic acid templates, polymerases and nucleotides to form a plurality of stabilized ternary complexes at a plurality of the features, wherein the stabilized ternary complexes each has a polymerase, template nucleic acid having a locus having a target allele, a locus-specific primer hybridized to the locus, and a next correct nucleotide that is a cognate to the target allele; and (c) detecting stabilized ternary complexes at the features, thereby identifying the target alleles.

The above embodiment uses locus-specific primers and allele-specific nucleotides. Alternatively, a method for identifying target alleles in a mixture of nucleic acids can use allele-specific primers. For example, the method can include steps of (a) providing an array of features, wherein different allele-specific primers are attached at different features of the array; (b) contacting the array with a plurality of nucleic acid templates, polymerases and nucleotides to form a plurality of stabilized ternary complexes at a plurality of the features, wherein the stabilized ternary complexes each has a polymerase, template nucleic acid having a target allele of a locus, an allele-specific primer hybridized to the locus, and a next correct nucleotide having a cognate in the locus, wherein the 3' end of the allele-specific primer has a cognate nucleotide for the target allele; and (c) detecting stabilized ternary complexes at the features, thereby identifying the target alleles.

In some embodiments, an array can be used that includes both allele-specific primers and locus-specific primers. Accordingly, this disclosure provides, a method for identifying target alleles in a mixture of nucleic acids that includes steps of (a) providing an array of features, wherein different locus-specific primers are attached at a first subset of the features of the array, and wherein different allele-specific primers are attached at a second subset of the features of the array; (b) contacting the array with a plurality of nucleic acid templates, polymerases and nucleotides to form a plurality of stabilized ternary complexes at a plurality of the features, wherein the stabilized ternary complexes at the first subset of features each has a polymerase, template nucleic acid having a target allele of a locus, a locus-specific primer hybridized to the locus, and a next correct nucleotide that is a cognate to the target allele, wherein the stabilized ternary complexes at the second subset of features each has a polymerase, template nucleic acid having a target allele of a locus, an allele-specific primer hybridized to the locus, and a next correct nucleotide having a cognate in the locus, and wherein the 3' end of the allele-specific primer has a cognate nucleotide for the target allele; and (c) detecting stabilized ternary complexes at the features, thereby identifying the target alleles.

Described herein are polymerase-based methods for detecting nucleic acids having target sequences of interest such as target alleles. Embodiments of the methods exploit the specificity with which a polymerase can form a stabilized ternary complex with the target allele and a cognate nucleotide for the allele. The stabilized ternary complex can include the polymerase, a primed nucleic acid template having the target allele, and a cognate nucleotide for the target allele. In particular embodiments, the cognate nucleotide is non-covalently bound to the stabilized ternary complex, interacting with the other members of the complex solely via non-covalent interactions. Useful methods and compositions for forming a ternary complex are set forth in further detail below and in commonly owned U.S. patent application Ser. Nos. 14/805,381, now published as U.S. Pub. No. 2017/0022553, and 62/375,379, which is incorporated by reference in U.S. Ser. No. 15/677,870, each of which is incorporated herein by reference.

While a ternary complex can form between a polymerase, primed template nucleic acid and next correct nucleotide in the absence of certain catalytic metal ions (e.g., $Mg^{2+}$), chemical addition of the nucleotide is inhibited in the absence of the catalytic metal ions. Low or deficient levels of catalytic metal ions, causes non-covalent (physical) sequestration of the next correct nucleotide in a stabilized ternary complex. Other methods disclosed herein also can be used to produce a stabilized ternary complex.

Optionally, a stabilized ternary complex can be formed when the primer of the primed template nucleic acid includes a blocking group that precludes enzymatic incorporation of an incoming nucleotide into the primer. The interaction can take place in the presence of stabilizers, whereby the polymerase-nucleic acid interaction is stabilized in the presence of the next correct nucleotide (i.e., stabilizers that stabilize the ternary complex). The primer of the primed template nucleic acid optionally can be either an extendible primer, or a primer blocked from extension at its 3'-end (e.g., by the presence of a reversible terminator moiety). The primed template nucleic acid, the polymerase and the cognate nucleotide are capable of forming a ternary complex when the base of the cognate nucleotide is complementary to the next base of the primed template nucleic acid.

As set forth above, conditions that favor or stabilize a ternary complex can be provided by the presence of a blocking group that precludes enzymatic incorporation of an incoming nucleotide into the primer (e.g. a reversible terminator moiety on the 3' nucleotide of the primer) or the absence of a catalytic metal ion. Other useful conditions include the presence of a ternary complex stabilizing agent such as a non-catalytic ion (e.g., a divalent or trivalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide) are provided by the presence of one or more monovalent cations and/or glutamate anions. As a further option, a polymerase engineered to have reduced catalytic activity or reduced propensity for binary complex formation can be used.

As set forth above, ternary complex stabilization conditions can accentuate the difference in affinity of polymerase toward primed template nucleic acids in the presence of different nucleotides, for example, by destabilizing binary complexes. Optionally, the conditions cause differential affinity of the polymerase for the primed template nucleic acid in the presence of different nucleotides. By way of example, the conditions include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate anions. Optionally, the source of glutamate ions can be potassium glutamate. In some instances, the concentrations of potassium glutamate that can be used to alter polymerase affinity of the primed template nucleic acid extend from 10 mM to 1.6 M of potassium glutamate, or any amount in between 10 mM and 1.6 M. As indicated above, high salt refers to a concentration of salt from 50 to 1,500 mM salt.

It will be understood that options set forth herein for stabilizing a ternary complex need not be mutually exclusive and instead can be used in various combinations. For example, a ternary complex can be stabilized by one or a combination of means including, but not limited to, crosslinking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, and other means set forth herein.

A ternary complex can be formed with any of a variety of nucleic acid template sequences in a method set forth herein. The methods are particularly useful for selectively detecting one allele at a genetic locus to distinguish it from one or more other alleles at the locus. Thus, a mixture of nucleic acid templates that is used in a method set forth herein can include one or more alleles at a particular locus. For example, the mixture can include first and second alleles, one of which is selectively detected. A mixture can include a variety of other nucleic acids, for example, some or all of the sequence content of a genome or exome from one or more organism.

Methods set forth herein can be particularly useful for selectively detecting a minor allele. The minor allele can be one of a pair occurring at a bi-allelic locus, one of three alleles at a tri-allelic locus or one of four alleles at a quad-allelic locus. The minor allele frequency of an allele selectively detected herein can be at most 40%, 25%, 10%, 5%, 0.5% or less. The methods can also be used to selectively detect alleles having higher frequency including, for example, major alleles. Exemplary alleles that can be detected include, without limitation, single nucleotide polymorphisms (SNPs), insertion-deletion (indel) polymorphisms and alternative splicing polymorphisms.

Although the methods of the present disclosure are particularly well suited to selectively detecting an allele at a multi-allelic locus, other sequences can also be detected. Thus, the methods and compositions exemplified for alleles can be extended to other sequences and other templates. For example, the methods can be used to detect a non-polymorphic sequence. In such cases the next correct nucleotide and primer need not correlate to a particular allele in the template. In other embodiments, the methods can be used to selectively detect a mutant sequence compared to its wild-type sequence or vice versa. This can be useful for example, when evaluating reagents for or products of protein engineering or synthetic biology.

Nucleic acid templates that are used in a method or composition herein can be DNA such as genomic DNA, synthetic DNA, amplified DNA, copy DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification product. Primers used herein can be DNA, RNA or analogs thereof.

Particularly useful nucleic acid templates are genome fragments that include sequences identical to a portion of a genome. A population of genome fragments can include at least 5%, 10%, 20%, 30%, or 40%, 50%, 60%, 70%, 75%, 80%, 85%, 90%, 95% or 99% of a genome. A genome fragment can have, for example, a sequence that is substantially identical to at least about 25, 50, 70, 100, 200, 300, 400, 500, 600, 700, 800, 900 or 1000 or more nucleotides of a genome. A genome fragment can be DNA, RNA, or an analog thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *pneumocystis carinii*, *Takifugu rubripes*, yeast, *Saccharamoyces cerevisiae* or *Schizosaccharomyces pombe*; or a *plasmodium falciparum*. Nucleic acids can also be derived from a prokaryote such as a bacterium, *Escherichia coli*, *staphylococci* or *mycoplasma pneumoniae*; an archae; a virus such as Hepatitis C virus or human immunodeficiency virus; or a viroid. Nucleic acids can be derived from a homogenous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. Nos. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

Particular embodiments of the methods set forth herein can use a native nucleotide, nucleotide analog or modified nucleotide. Such nucleotides can be used, for example, for forming a stabilized ternary complex. Optionally, a nucleotide analog has a nitrogenous base, five-carbon sugar, and phosphate group; wherein any moiety of the nucleotide may be modified, removed and/or replaced. Nucleotide analogs may be non-incorporable nucleotides. Such nucleotides that are incapable of incorporation include, for example, monophosphate and diphosphate nucleotides. In another example, the nucleotide may contain modification(s) to the triphosphate group that make the nucleotide non-incorporable. Examples of non-incorporable nucleotides may be found in U.S. Pat. No. 7,482,120, which is incorporated by reference herein. Non-incorporable nucleotides may be subsequently modified to become incorporable. Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein.

Nucleotide analogs can include terminators that reversibly prevent nucleotide incorporation at the 3'-end of the primer after the analog has been incorporated. For example, U.S. Pat. Nos. 7,544,794 and 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include those described in U.S. Pat. Nos. 7,956,171, 8,071,755, and 9,399,798 (the disclosures of these U.S. patents are incorporated herein by reference). In certain embodiments, a reversible blocking moiety can be removed from a primer, allowing for nucleotide incorporation. Compositions and methods for deblocking are set forth in the above references.

Alternatively, nucleotide analogs irreversibly prevent nucleotide incorporation at the 3'-end of the primer to which they have been incorporated. Irreversible nucleotide analogs include 2',3'-dideoxynucleotides (ddNTPs such as ddGTP, ddATP, ddTTP, ddCTP). Dideoxynucleotides lack the 3'-OH group of dNTPs that is essential for polymerase-mediated primer extension.

Optionally, a nucleotide (e.g. a native nucleotide or nucleotide analog) is present in a mixture during formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 nucleotide types in a template nucleic acid. Alternatively or additionally, one or more nucleotide types that are present can be complementary to at most 4, 3, 2, or 1 nucleotide types in a template nucleic acid.

Any nucleotide modification that stabilizes a polymerase in a ternary complex may be used in the methods disclosed herein. The nucleotide may be bound permanently or transiently. Optionally, a nucleotide analog is fused to a polymerase. Optionally, a plurality of nucleotide analogs are fused to a plurality of polymerases, wherein each nucleotide analog is fused to a different polymerase. Optionally, a nucleotide that is present in a stabilized ternary complex is not the means by which the ternary complex is stabilized. Accordingly, any of a variety of other ternary complex stabilization methods may be combined in a reaction utilizing a nucleotide analog.

In particular embodiments, the primer strand of a primed template nucleic acid molecule undergoing one or more steps of a method set forth herein is chemically unchanged by the polymerase. This is to say that the primer is neither extended by formation of a new phosphodiester bond, nor shortened by nucleolytic degradation during the examination step to identify the next correct nucleotide.

Polymerases that may be used to carry out a method of the present disclosure include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. Optionally, the naturally occurring and/or modified variations thereof have the ability to catalyze a polymerization reaction. Optionally, the naturally-occurring and/or modified variations have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, enhanced catalysis rates, reduced catalysis rates, catalytic inactivity etc. Mutant polymerases include, for example, polymerases wherein one or more amino acids are replaced with other amino acids, or insertions or deletions of one or more amino acids.

Modified polymerases include polymerases that contain an exogenous label moiety (e.g., an exogenous fluorophore), which can be used to detect the polymerase. Optionally, the label moiety can be attached after the polymerase has been at least partially purified using protein isolation techniques. For example, the exogenous label moiety can be chemically linked to the polymerase using a free sulfhydryl or a free amine moiety of the polymerase. This can involve chemical linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP) or wavelength shifted variants of GFP.

Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated herein by reference.

Useful RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

Useful reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

A stabilized ternary complex, or a component that is capable of forming (i.e. participating in the formation of) a ternary complex, can be attached to a solid support. The solid support can be made from any of a variety of materials set forth herein, for example, above in the definitions or below. Suitable materials may include glass, polymeric materials, silicon, quartz (fused silica), borofloat glass, silica, silica-based materials, carbon, metals, an optical fiber or bundle of optical fibers, sapphire, or plastic materials. The particular material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein; or ease of manipulation or low cost of manufacture.

A particularly useful solid support is a particle such as a bead or microsphere as exemplified below. Populations of beads can be used for attachment of populations of stabilized ternary complexes or components capable of forming the complexes (e.g. polymerases, templates, primers or nucleotides). In some embodiments, it may be useful to use a configuration whereby each bead has a single type of stabilized ternary complex or a single type of component capable of forming the complex. For example, an individual bead can be attached to a single type of ternary complex, a single type of template allele, a single type of allele-specific primer, a single type of locus-specific primer or a single type of nucleotide. Alternatively, different types of components need not be separated on a bead-by-bead basis. As such, a single bead can bear multiple different types of ternary complexes, template alleles, allele-specific primers, locus-specific primers and/or nucleotides. The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, bead or microsphere also can correspond to a wide variety of different forms and shapes. For example, they can be symmetrically shaped (e.g. spherical or cylindrical) or irregularly shaped (e.g. controlled pore glass). In addition, beads can be porous, thus increasing the surface area available for capture of ternary complexes or components thereof. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pub. Nos. 2004/0263923, 2004/0233485, 2004/0132205, or 2004/0125424, each of which is incorporated herein by reference.

As will be recognized from the above bead array embodiments, a method of the present disclosure can be carried out in a multiplex format whereby multiple different types of nucleic acids are detected in parallel in a method set forth herein. Although it is also possible to serially process different types of nucleic acids using one or more steps of the methods set forth herein, parallel processing can provide cost savings, time savings and uniformity of conditions.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Nucleic acid arrays can be configured such that the nucleic acids that are attached at the features have a 3' end that is accessible to interaction with a polymerase. In such embodiments, the 3' end of the attached primer can participate in ternary complex formation, or polymerase catalyzed extension or both. For example, primers can be attached to features via the 5' end of the primer or at another portion of the primer that does not sterically block interaction of the 3' end with a polymerase. Examples of primers that are attached via their 5' ends are diagrammed in FIG. 2 and FIG. 3.

Although several embodiments set forth herein are exemplified using an array of primers that interact directly with a polymerase, it will be understood that the primer of the array can serve as a probe that hybridizes to other nucleic acids, these other nucleic acids providing a 3' end that interacts with a polymerase. For example, primers can be attached to array features via their 3' ends. In such cases, a complementary nucleic acid strand can be hybridized to the primer and a polymerase can interact with the 3' end of the complementary nucleic acid strand. Complementary nucleic acid strands can be hybridized to array primers independent of the end of the primer that is attached to the array. Furthermore, a complementary nucleic acid can be hybridized to an array primer to form a linker or splint to which a third nucleic acid strand hybridizes. The third nucleic acid strand can have a free 3' end that interacts with a polymerase to form a stabilized ternary complex, to participate in primer extension or both. An advantage to using a configuration where one or more complementary nucleic acids is hybridized to an array primer is to preserve the array against unwanted modification. For example, a polymerase extension step can be used to modify the 3' end of a nucleic acid that is hybridized to an array primer. Then the modified nucleic acid can be removed and the array re-used in a similar assay. However, had the arrayed primer been modified by extension it may have been effectively spent and unusable for further assay.

In some embodiments, the array can be configured as a tiling array. A tiling array can be used to probe intensively for sequences that are known to exist in a contiguous region. Tiling arrays can be configured such that most, or all, of the sequence of the contiguous region is aligned to sequences of the primers attached to the array. As such, the array provides a relatively high sequence resolution for the contiguous region. Exemplary tiling arrays include those that are commercially available such as the GeneChip® Human Tiling 2.0R Array Set (Affymetrix, Santa Clara, Calif.). Although tiling arrays have been useful, their accuracy has relied upon relatively narrow parameters for probe design and a narrow range of hybridization conditions to provide detection specificity. The methods of the present disclosure provide the advantage of improved specificity based on the increased level of specificity for a target sequence that is provided by ternary complex formation compared to merely relying on hybridization complementarity to distinguish primers that are nearest neighbors when aligned to the target sequence or primers that bind different alleles in the target sequence.

In some embodiments of the present methods, a sample that is contacted with a tiled array can contain nucleic acid fragments that are derived from a contiguous nucleic acid, and the primers are tiled with respect to the contiguous sequence. For example, the contiguous nucleic acid can be enzymatically or physically fragmented or fragment amplicons can be copied from the contiguous nucleic acid. In some embodiments, the contiguous sequence is a genomic sequence and the mixture of nucleic acids are fragments of the genomic sequence. Other contiguous sequences set forth herein or known in the art can be used. The plurality of primers on the array can be tiled at a resolution that results in nearest neighbor primer sequences that are adjacent in an alignment to the contiguous sequence being separated by a predefined average gap (e.g. a gap of at most 10 nucleotides). Alternatively or additionally, nearest neighbor primer sequences can overlap each other when n aligned to the contiguous sequence (e.g. the overlap between primers can be at least 1 nucleotide).

Other useful arrays include those that are used in nucleic acid sequencing applications. For example, arrays that are used to attach amplicons of genomic fragments (often referred to as clusters) can be particularly useful. Examples of nucleic acid sequencing arrays that can be modified for use herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

Accordingly, an embodiment is provided wherein template nucleic acids are attached to an array. For example, a method for identifying target alleles in a mixture of nucleic acids can include steps of (a) providing an array of features, wherein different template nucleic acids are attached to different features of the array; (b) contacting the array with a plurality of primers, polymerases and nucleotides to form a plurality of stabilized ternary complexes at a plurality of the features, wherein the stabilized ternary complexes at the features each has a polymerase, a template nucleic acid attached to a feature of the array and having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (c) detecting stabilized ternary complexes at the features, thereby identifying the target alleles.

As set forth above, embodiments of the methods that employ attached nucleic acids can use arrays that are known in the art and in some cases arrays that are commercially available. Moreover, linkages made from commercial arrays (or other nucleic acid arrays) to nucleic acid probes can be replaced with linkages for attaching polymerases or nucleotides to surfaces. In other embodiments, polymerases or nucleotides can be attached to oligonucleotide moieties that are complementary to probes located on nucleic acid arrays. In such embodiments, the nucleotide or polymerase can be attached to the surface via hybridization or crosslinking of the complementary strands.

A stabilized ternary complex or component that is used to make such a complex can be attached to an array or other solid support using any of a variety of methods well known in the art. Such methods include for example, attachment by direct chemical synthesis onto the solid support, chemical attachment, photochemical attachment, thermal attachment, enzymatic attachment and/or absorption. These and other methods are well known in the art and applicable for attachment of proteins, nucleotides or nucleic acids in any of a variety of formats and configurations. Attachment to a solid support can occur via a covalent linkage or via non-covalent interactions. Exemplary non-covalent interactions are those between a ligand-receptor pair such as streptavidin (or analogs thereof) and biotin (or analogs thereof) or between an antibody (or functional fragment thereof such as a Fab or ScFv) and epitope. Other useful receptor-ligand pairs include lectin and carbohydrate, and complementary first and second strands of a double-stranded nucleic acid.

Other chemistry conditions and linkages that are useful are those known as "click chemistry" (e.g. U.S. Pat. Nos. 6,737,236 and 7,427,678, each incorporated herein by reference in its entirety). Also useful are azide alkyne Huisgen cycloaddition reactions, which use a copper catalyst (e.g. U.S. Pat. Nos. 7,375,234 and 7,763,736, each incorporated herein by reference in its entirety). Copper-free Huisgen reactions ("metal-free click") using strained alkynes can be employed. Other useful linkage chemistries include, but are not limited to triazine-hydrazine moieties which can link to aldehyde moieties, for example, as described in U.S. Pat. No. 7,259,258, which is incorporated by reference; triazine chloride moieties which can link to amine moieties; carboxylic acid moieties which can link to amine moieties using a coupling reagent, such as EDC; thiol moieties which can link to thiol moieties; alkene moieties which can link to dialkene moieties that are coupled through Diels-Alder reactions; and acetyl bromide moieties which can link to thiophosphate moieties, such as those described in WO 2005/065814, which is incorporated by reference. Glass-like surfaces can also be modified with various glass-reactive molecules, such as functionalized silanes, some of which are commercially available through Gelest, Inc.

In particular embodiments, a stabilized ternary complex, polymerase, nucleic acid or nucleotide is attached to a flow cell surface or to a solid support in a flow cell. A flow cell allows convenient fluidic manipulation by passing solutions into and out of a fluidic chamber that contacts the support-bound, ternary complex. The flow cell also provides for detection of the fluidically manipulated components. For example, a detector can be positioned to detect signals from the solid support, such as signals from a label that is recruited to the solid support due to formation of a stabilized ternary complex. Exemplary flow cells that can be used are described, for example, in US Pat. App. Publ. No. 2010/0111768 A1, WO 05/065814 and U.S. Pat. App. Publ. No. 2012/0270305 A1, each of which is incorporated herein by reference.

Polymerase molecules can be attached to an array used for identifying target alleles. For example, a method for identifying target alleles in a mixture of nucleic acids can include steps of (a) providing an array of features, wherein polymerases are attached at features of the array; (b) contacting the array with a plurality of primers, template nucleic acids and nucleotides to form a plurality of stabilized ternary complexes at a plurality of the features, wherein the stabilized ternary complexes at the features each has a polymerase that is attached at a feature of the array, template nucleic acid having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (c) detecting stabilized ternary complexes at the features, thereby identifying the target alleles.

A method set forth herein can include a step of contacting an array of features with components that form a stabilized ternary complex at one or more features. As exemplified above, and elsewhere herein, different components of a stabilized ternary complex can be attached to a feature of an array. The other components that participate in formation of a stabilized ternary complex can be provided in solution. For example, if primers are attached at the features, stabilized ternary complexes can be formed by providing template nucleic acids, polymerases and next correct nucleotides in solution. For embodiments where template nucleic acids are attached to the features, stabilized ternary complexes can be formed by providing primers, polymerases and next correct nucleotides in solution. In other embodiments, ternary complexes can be formed between feature-attached nucleotides and fluidically delivered polymerases, templates and primers.

The components that are provided in solution can be delivered simultaneously in a mixture, or alternatively, the components can be delivered sequentially. In an example of sequential delivery, the solution components can be delivered sequentially until a mixture of all solution-based components is created. In an alternative example, the solution components can be delivered and removed sequentially. For example, primer-template hybrids can be formed at the features of an array, then binary complexes can be formed by delivering polymerases in solution, then ternary complexes can be formed by delivering next correct nucleotides in solution. In the latter example, optional washes can be performed to remove unbound solution components before a subsequent component is delivered.

A ternary complex that is made or used in accordance with the present disclosure may optionally include one or more exogenous label(s). The label can be present on the polymerase, template nucleic acid, primer and/or cognate nucleotide. Typically, the labeled component is delivered in solution and then recruited to a feature where a ternary complex is formed on an attached component. Exogenous labels can be useful for detecting a ternary complex or an individual component thereof, during one or more of the manipulations set forth herein. Exemplary labels, methods for attaching labels and methods for using labeled components are set forth in commonly owned U.S. patent application Ser. Nos. 14/805,381, now published as U.S. Pub. No. 2017/0022553 A1, and 62/375,379, which is incorporated by reference in U.S. Ser. No. 15/677,870, each of which is incorporated herein by reference.

Further examples of useful exogenous labels include, but are not limited to, radiolabel moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore moieties include, but are not limited to umbelliferone, fluorescein, isothiocyanate, rhodamine, tetramethyl rhodamine, eosin, green fluorescent protein, erythrosin, coumarin, methyl coumarin, pyrene, malachite green, stilbene, lucifer yellow™, Cascade Blue™, Texas Red™, dansyl chloride, phycoerythrin, phycocyanin, fluorescent lanthanide complexes such as those including Europium and Terbium, Cy3, Cy5, and others known in the art as described, for example, in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

A secondary label can be used in a method of the present disclosure. A secondary label is a binding moiety that can bind specifically to a labeled partner moiety. For example, a ligand moiety can be attached to a polymerase, nucleic acid or nucleotide to allow detection via specific affinity for labeled receptor. Exemplary pairs of binding moieties that can be used include, without limitation, antigen and immunoglobulin or active fragments thereof, such as FAbs; immunoglobulin and immunoglobulin (or active fragments, respectively); avidin and biotin, or analogs thereof having specificity for avidin; streptavidin and biotin, or analogs thereof having specificity for streptavidin; or carbohydrates and lectins.

In some embodiments, the secondary label can be a chemically modifiable moiety. In this embodiment, labels having reactive functional groups can be incorporated into a stabilized ternary complex. The functional group can be subsequently covalently reacted with a primary label moiety. Suitable functional groups include, but are not limited to, amino groups, carboxy groups, maleimide groups, oxo groups and thiol groups.

In alternative embodiments, a ternary complex can lack exogenous labels. For example, a ternary complex and components used in the formation of the ternary complex (e.g. polymerase, template nucleic acid, primer and/or cognate nucleotide) can lack one, several or all of the exogenous labels described herein or in the above-incorporated references. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. patent application. Ser. Nos. 14/805,381, now published as U.S. Pub. No. 2017/0022553, and 62/375,379, which is incorporated by reference in U.S. Ser. No. 15/677,870, each of which is incorporated herein by reference.

An appropriate spatial distribution of attached components coupled with an appropriate distribution of labels on solution components can be used to create an array of stabilized ternary complexes that is useful for identifying alleles at one or more loci of a nucleic acid sample. In some embodiments, it may be useful to use a configuration whereby each feature has a single type of stabilized ternary complex (e.g. one allele type per feature). As such, alleles can be distinguished based on spatial location on the array instead of or in addition to the use of different labels for different alleles. Alternatively, different stabilized ternary complexes need not be separated on a feature-by-feature basis. As such, a feature can bear multiple different types of stabilized ternary complexes (e.g. multiple types of alleles per feature) that can optionally be distinguished based on different types of labels that associate with different types of alleles, respectively.

In some embodiments, the method for identifying target alleles in a mixture of nucleic acids can include steps of (a) providing an array of features, wherein different locus-specific primers are attached at different features of the array; (b) contacting the array with a plurality of nucleic acid templates, polymerases and nucleotides to form a plurality of stabilized ternary complexes at a plurality of the features, wherein the nucleotides have exogenous labels, wherein the stabilized ternary complexes each has a polymerase, template nucleic acid having a target allele of a locus, a locus-specific primer hybridized to the locus, and a next correct nucleotide that is a cognate to the target allele; and (c) detecting stabilized ternary complexes at the features by detecting the exogenous labels, thereby identifying the target alleles.

In one configuration of the above embodiment, at least two types of nucleotides are contacted with the array in step (b), and the different exogenous labels distinguish at least two alleles at each locus in step (c). As exemplified in FIG. 3 the two types of labels can be used to distinguish two alleles that are present at the same feature of an array. In an alternative configuration, a single type of nucleotide can be contacted with the array in step (b). Other types of nucleotides need not be contacted with the array in this embodiment. However, optionally one or more other types of nucleotides can be sequentially contacted with the array. Sequentially added nucleotides can be detected sequentially such that the order of addition coupled with appearance of new signal can be used to distinguish newly formed, stabilized ternary complexes, whether or not the sequentially added nucleotide types have mutually distinguishable labels. Alternatively, sequentially added nucleotides can be detected after multiple additions are complete.

In some embodiments, a method for identifying target alleles in a mixture of nucleic acids can include steps of (a) providing an array of features, wherein different locus-specific primers are attached at different features of the array; (b) contacting the array with a plurality of nucleic acid templates, polymerases and nucleotides to form a plurality of stabilized ternary complexes at a plurality of the features, wherein the polymerases have exogenous labels, wherein the stabilized ternary complexes each has a polymerase, template nucleic acid having a target allele of a locus, a locus-specific primer hybridized to the locus, and a next correct nucleotide that is a cognate to the target allele; and (c) detecting stabilized ternary complexes at the features by detecting the exogenous labels, thereby identifying the target alleles. In some configurations, a single type of nucleotide is contacted with the array in step (b). Other types of nucleotides need not be contacted with the array in this embodiment. However, optionally one or more other types of nucleotides can be sequentially contacted with the array. Again, detection can be carried out sequentially as different nucleotides are incorporated into ternary complexes or detection can occur after multiple nucleotide additions.

In some embodiments, a method for identifying target alleles in a mixture of nucleic acids includes steps of (a) providing an array of features, wherein different allele-specific primers are attached at different features of the array; (b) contacting the array with a plurality of nucleic acid templates, polymerases and nucleotides to form a plurality of stabilized ternary complexes at a plurality of the features, wherein the nucleotides have exogenous labels, wherein the stabilized ternary complexes each have a polymerase, template nucleic acid having a target allele of a locus, an allele-specific primer hybridized to the locus, and a next correct nucleotide having a cognate in the locus, wherein the 3' end of the allele-specific primer has a cognate nucleotide for the target allele; and (c) detecting stabilized ternary complexes at the features by detecting the exogenous labels, thereby identifying the target alleles.

In one configuration of the above embodiment, at least two types of nucleotides are contacted with the array in step (b), and the at least two types of nucleotides have exogenous labels that are not distinguished from each other in step (c). As exemplified in FIG. 2 the allele-specific primers can be present at different feature of the array such that the alleles are distinguished by spatial location rather than differences in the type of nucleotide that is recruited to form ternary complexes at the features. Nevertheless, if desired, two or more types of nucleotides can have distinguishable labels. In an alternative configuration, a single type of nucleotide can be contacted with the array in step (b). Other types of nucleotides need not be contacted with the array in this embodiment. However, optionally one or more other types of nucleotides can be sequentially contacted with the array. Again, detection can be carried out sequentially as different nucleotides are incorporated into ternary complexes or detection can occur after multiple nucleotide additions.

Optionally, the provided methods further include a wash step. The wash step can occur before or after any other step in the method. For example, a method set forth herein can optionally include a step of washing a solid support after forming one or more stabilized ternary complexes. The wash can provide the advantage of removing contaminants such as components of a mixture from which one or more components of the stabilized ternary complex were derived. In particular embodiments, the wash step occurs under conditions that stabilize the ternary complex. For example, one or more of the stabilizing conditions or stabilizing agents set forth elsewhere herein can be employed during a wash step. Optionally, the wash solution includes nucleotide(s) of the same type as the next correct nucleotide(s) used during formation of the stabilized ternary complex. Including the next correct nucleotide(s) at a sufficient concentration can provide the advantage of stabilizing previously formed ternary complexes from unwanted disassociation. This in turn prevents unwanted reduction in detection sensitivity due to washing away previously formed ternary complexes. Optionally, the ternary complex has a half-life and the wash step is performed for a duration shorter than the half-life of the ternary complex.

A method of the present disclosure can include a detection step. Generally, detection can be achieved by methods that perceive properties that are intrinsic to label moieties. Exemplary properties upon which detection can be based include, but are not limited to, mass, electrical conductivity, energy absorbance, fluorescence or the like. Detection of fluorescence can be carried out using methods known in the art pertaining to nucleic acid arrays. A fluorophore can be detected based on any of a variety of fluorescence phenomena including, for example, emission wavelength, excitation wavelength, fluorescence resonance energy transfer (FRET) intensity, quenching, anisotropy or lifetime. Other detection techniques that can be used in a method set forth herein include, for example, mass spectrometry which can be used to perceive mass; surface plasmon resonance which can be used to perceive binding to a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques. Further techniques for detecting labels on an array are set forth, for example, in commonly owned U.S. Ser. Nos. 14/805,381, now published as U.S. Pub. No. 2017/0022553; and 62/375,379, which is incorporated by reference in U.S. Ser. No. 15/677,870 or in U.S. Pat. Nos. 6,355,431 or 9,045,796, each of which is incorporated herein by reference.

A target allele or other target sequence can be distinguished from other alleles using an iterative method whereby particular steps of a method set forth herein are repeated. The methods set forth herein are well suited to iteration because the nucleic acid primer need not be consumed or modified following use to detect a target allele. This contrasts with other methods of allele detection where a primer is extended to incorporate a labeled nucleotide. Once the primer has been extended it has been spent and must be replaced or chemically reverted for use in a repetition of the primer extension step.

An advantage of the iterative approach provided by the current disclosure is that each iteration can add confidence in identification of one or more target alleles improving discrimination from other biological materials including other nucleic acids having similar sequences (e.g. other alleles at the same locus of each target allele). The reagents can be re-used thereby providing a cost- and time-effective alternative to other methods that consume primers and other reagents.

Accordingly, a method for identifying target alleles in a mixture of nucleic acids can include steps of (a) providing an array of features, wherein different locus-specific primers are attached at different features of the array; (b) contacting the array with a plurality of nucleic acid templates, polymerases and nucleotides to form a plurality of stabilized ternary complexes at a plurality of the features, wherein the stabilized ternary complexes each has a polymerase, template nucleic acid having a target allele of a locus, a locus-specific primer hybridized to the locus, and a next correct nucleotide that is a cognate to the target allele; (c) detecting stabilized ternary complexes at the features, thereby identifying the target alleles, and (d) dissociating the next correct nucleotide from each feature of the array after the detecting of the stabilized ternary complexes, whereby the ternary complex at each of the features is converted to a binary complex including the polymerase, the template nucleic acid and the locus-specific primer from the ternary complex that was at the feature. Optionally, step (d) can further include dissociating the polymerases from the array after the detecting of the stabilized ternary complexes, whereby the ternary complex at each of the features is converted to a double stranded nucleic acid consisting of the template nucleic acid and the locus-specific primer from the ternary complex that was at the feature.

As a further option, after step (d) the method can include a step (e) forming a second plurality of stabilized ternary complexes at a plurality of the features, wherein each of the features includes the template nucleic acid and the locus-specific primer from the ternary complex that was at the feature, a polymerase and a next correct nucleotide that is a cognate to the target allele of the template nucleic acid. If desired, the method can also include a step: (f) detecting stabilized ternary complexes of the second plurality at the features, thereby identifying the target alleles.

In particular embodiments of the above method, the same polymerase molecule is retained at each of the features from step (b) to step (f). However, if desired different polymerases can be delivered at one or more of the intervening steps.

In some embodiments of the above method, a first type of nucleotide has a first type of exogenous label in step (c) and the first type of nucleotide has a second type of exogenous label in step (f).

Different combinations of labels can be used. For example, step (c) of the method can include detecting a first type of exogenous label on a first type of nucleotide, a second type of exogenous label on a second type of nucleotide, a third type of exogenous label on a third type of nucleotide and a fourth type of exogenous label on a fourth type of nucleotide.

Alternatively, step (c) of the method can include detecting a first type of exogenous label on a first type of nucleotide, the first type of exogenous label on a second type of nucleotide, a second type of exogenous label on a third type of nucleotide and the second type of exogenous label on a fourth type of nucleotide. Optionally, step (f) can be carried out by detecting the second type of exogenous label on the first type of nucleotide, the second type of exogenous label on the second type of nucleotide, the first type of exogenous label on the third type of nucleotide and the first type of exogenous label on the fourth type of nucleotide.

As a further alternative, the same type of label can be used on two or more nucleotide types, or, if different labels are used, they can produce non-distinguishable signals under the detection conditions employed.

In another iterative approach, a method for identifying target alleles in a mixture of nucleic acids can include steps of (a) providing an array of features, wherein different allele-specific primers are attached at different features of the array; (b) contacting the array with a plurality of nucleic acid templates, polymerases and nucleotides to form a plurality of stabilized ternary complexes at a plurality of the features, wherein the stabilized ternary complexes each has a polymerase, template nucleic acid having a target allele of a locus, an allele-specific primer hybridized to the locus, and a next correct nucleotide having a cognate in the locus, wherein the 3' end of the allele-specific primer has a cognate nucleotide for the target allele; (c) detecting stabilized ternary complexes at the features, thereby identifying the target alleles, and (d) dissociating the next correct nucleotide from each feature of the array after the detecting of the stabilized ternary complexes, whereby the ternary complex at each of the features is converted to a binary complex comprising the polymerase, the template nucleic acid and the allele-specific primer from the ternary complex that was at the feature. Optionally, step (d) can further include dissociating the polymerases from the array after the detecting of the stabilized ternary complexes, whereby the ternary complex at each of the features is converted to a complex including the template nucleic acid and the allele-specific primer from the ternary complex that was at the feature.

As a further option, after step (d) the method can include a step: (e) forming a second plurality of stabilized ternary complexes at a plurality of the features, wherein each of the features includes the template nucleic acid and the allele-specific primer from the ternary complex that was at the feature, a polymerase and a next correct nucleotide that is a cognate to the target allele of the template nucleic acid. If desired, the method can also include a step: (f) detecting stabilized ternary complexes of the second plurality at the features, thereby identifying the target alleles.

In particular embodiments of the above method, the same polymerase molecule is retained at each of the features from step (b) to step (f). However, if desired different polymerases can be delivered at one or more of the intervening steps.

As exemplified above, a method of the present disclosure can further include a step of dissociating a ternary complex from a solid support. Optionally, dissociation can be carried without covalently adding the next correct nucleotide to the 3' end of the primer. This can be achieved by maintaining ternary complex stabilization until the ternary complex is released. An advantage of releasing unmodified primer is that the primer can be re-used for detecting the same type of allele. For example, the primer can be used in an iterative method to recapture the same allele as set forth above. The primer can also be used with a new mixture of nucleic acids to detect a new template nucleic acid having the same type of allele.

Exemplary dissociation techniques include, but are not limited to, denaturation of the polymerase, competitive binding of a different nucleic acid to the polymerase to cause release of the target allele, incubation of the ternary complex in a solution that is devoid of next correct nucleotide, in a solution that is devoid of primed template, or in a solution having a concentration of next correct nucleotide or primed template that is substantially below the dissociation constant ($K_d$) of the polymerase for the next correct nucleotide or primed template, respectively. In some embodiments, the ternary complex can be incubated with a nucleotide that is different from the next correct nucleotide (e.g. a cognate nucleotide for a different allele than the target allele). This dissociation method provides an advantage of being relatively gentle and specific such that dissociation of the desired allele is selected over other alleles that may be present as contaminants.

In some embodiments, dissociation of a first ternary complex can be carried out by replacing a first labeled component of the complex with a second labeled component of the same type, wherein the second labeled component has a different label that is distinguishable from the first labeled component. For example, a ternary complex that was formed with a nucleotide type having a first label can be replaced with a nucleotide of the same type that has a second label. This will result in an apparent label exchange at a feature of an array where the ternary complex resides. Detection of the two labels can provide increased confidence in the accuracy of allele identification compared to the detection of only one label in the complex.

Alternatively, a step of dissociating a ternary complex can be carried out by extending the primer to incorporate a next correct nucleotide. The nucleotide that is incorporated can be a nucleotide molecule that was present in the stabilized ternary complex when it was formed in a mixture. Alternatively, a different nucleotide molecule can enter the ternary complex and then be incorporated into the primer. Thus, the incorporation step can involve replacing a nucleotide from a prior step and incorporating another nucleotide into the 3'-end of the primer. The incorporation step can involve releasing a nucleotide from within a ternary complex and incorporating a nucleotide of a different kind into the 3'-end of the primer.

The incorporation step can be carried out to add a labeled nucleotide. The labeled nucleotide can then be detected, for example, after detecting and dissociating the ternary complex. An advantage of incorporating a labeled nucleotide after detecting a ternary complex is that two different types of assays, detection of a ternary complex and detection of an extension product, can provide added confidence in identifying an allele compared to performing only one of the assays. Exemplary methods for performing extension assays on solid supports such as arrays are set forth in U.S. Pat. Nos. 6,355,431 or 9,045,796, each of which is incorporated herein by reference. The methods set forth herein can be used to replace or augment the extension assays set forth in the reference.

In some embodiments, only a single nucleotide is incorporated at the 3'-end of the primer. For example, the 3' position of the nucleotide can be modified to include a 3' terminator moiety. The 3' terminator moiety may be a reversible terminator or may be an irreversible terminator. Optionally, the reversible terminator nucleotide includes a 3'-$ONH_2$ moiety attached at the 3' position of the sugar moiety. Further examples of useful reversible terminator moieties are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and U.S. 2008/0108082, each of which is incorporated herein by reference. Optionally, multiple nucleotides are incorporated at the 3'-end of the primer. For example, the nucleotide that is incorporated can include a 3'-hydroxyl group that is capable of being further extended after incorporation. In some embodiments, the incorporation step is part of a sequencing technique, amplification technique, or other technique carried out using a nucleic acid for which an allele has been detected using a method set forth herein.

Incorporated nucleotides alternatively can be unlabeled nucleotides, or detectably labeled nucleotide analogs. Whether labeled or not, the nucleotides can be terminator nucleotides that are permanently or reversibly prevented from being extended once incorporated into a primer. The polymerase can dissociate from primed template after nucleotide incorporation. Exemplary reagents and conditions for incorporating nucleotides into the primed template of a ternary complex are set forth in commonly owned U.S. Ser. Nos. 14/805,381, now published as U.S. Pub. No. 2017/0022553, and 62/375,379, which is incorporated by reference in U.S. Ser. No. 15/677,870, each of which is incorporated herein by reference.

One or more template nucleic acids that are detected using a method of the present disclosure can be used in a variety of subsequent applications. For example, the template nucleic acid(s) can be used in a preparative method such as cloning of a gene or gene fragment. The template can be amplified using a method such as polymerase chain reaction (PCR), rolling circle amplification (RCA), multiple displacement amplification (MDA) or the like. In some cases, the primer that was used to form the ternary complex in a detection method can also be used for amplification. Generally, a template that is detected using a method set forth herein can be manipulated using methods known in the art including, but not limited to, those described in Sambrook et al., *Molecular Cloning: A Laboratory Manual,* 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

In particular embodiments, one or more template nucleic acid(s) that are detected using a method set forth herein can be used in another analytical method, for example, real time polymerase chain reaction (rtPCR), quantitative PCR (qPCR), nucleic acid sequencing, single-base extension genotyping or the like. Several of these methods employ a step of extending a primer along a template to be analyzed. In some cases, the primer that was used to form the ternary complex in a detection method set forth herein can also be used for primer extension in another analytical technique.

Optionally, sequencing is carried out as described in commonly owned U.S. Ser. No. 14/805,381, now published as U.S. Pub. No. 2017/0022553, which is incorporated herein by reference. Briefly, methods for determining the sequence of a template nucleic acid molecule can be based on formation of a ternary complex (between polymerase, primed nucleic acid and cognate nucleotide) under specified conditions. The method can generally include an examination step prior to incorporation of a nucleotide. The examination step can involve providing a template nucleic acid molecule primed with a primer; contacting the primed template nucleic acid molecule with a first reaction mixture that includes a polymerase and at least one nucleotide molecule; monitoring the interaction of the polymerase with the primed template nucleic acid molecule in the presence of the nucleotide molecule, without chemical incorporation of the nucleotide molecule into the primed template nucleic acid; and identifying a next base in the template nucleic acid using the monitored interaction of the polymerase with the primed template nucleic acid molecule in the presence of the nucleotide molecule. In this procedure, ternary complex stabilization and binary complex destabilization advantageously enhance discrimination between correct and incorrect nucleotides.

Sequencing-by-synthesis (SBS) techniques can also be used. SBS generally involves the enzymatic extension of a nascent primer through the iterative addition of nucleotides against a template strand to which the primer is hybridized. SBS can utilize nucleotide monomers that have a terminator moiety or those that lack any terminator moieties. Methods utilizing monomers having terminators include, for example, those described in WO 04/018497, U.S. Pat. No. 7,057,026, WO 91/106678, WO 07/123744, U.S. 2007/0166705, U.S 2006/0188901, U.S. 2006/0240439, U.S. 2006/0281109, WO 05/065814, U.S. 2005/0100900, WO 06/064199 or WO 07010251, the disclosures of which are incorporated herein by reference. Also useful are SBS methods that are commercially available from Illumina, Inc., San Diego Calif.

Some SBS embodiments include detection of a proton released upon incorporation of a nucleotide into an extension product. For example, sequencing based on detection of released protons can use an electrical detector and associated techniques that are commercially available from Thermo Fisher (Waltham, Mass.) or sequencing methods and systems described in U.S. Pat. App. Pub. Nos. 2009/0026082 A1; 2009/0127589 A1; 2010/0137143 A1; or 2010/0282617 A1, each of which is incorporated herein by reference.

Other sequencing procedures can be used, such as pyrosequencing. Pyrosequencing detects the release of inorganic pyrophosphate (PPi) as particular nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system.

Sequencing-by-ligation reactions are also useful including, for example, those described in Shendure et al. *Science* 309:1728-1732 (2005); U.S. Pat. Nos. 5,599,675; and 5,750,341, each of which is incorporated herein by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); and WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template.

Some embodiments can utilize methods involving the real-time monitoring of DNA polymerase activity. For example, nucleotide incorporations can be detected through fluorescence resonance energy transfer (FRET) interactions between a fluorophore-bearing polymerase and gamma-phosphate-labeled nucleotides, or with zeromode waveguides (ZMW). Techniques and reagents for sequencing via FRET and or ZMW detection are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

In some embodiments, sequencing methods utilize a polymerase that is attached to a ZMW or other solid-support feature. A ternary complex that is captured in a method set forth herein, or a component thereof, can be attached to a ZMW or other solid support used in sequencing techniques set forth above or otherwise known in the art.

Although the present disclosure has exemplified detection of nucleic acids in a multiplex format, it will be understood that single-plex detection can be similarly carried out. For example, a multiplex array set forth herein can be replaced with a solid support that attaches ternary complex formed with only one locus or only one allele. Furthermore, detection need not necessarily be carried out on a solid support and can instead be performed in a fluid such as a fluid in a vessel, tube or channel.

The methods of the present disclosure can be used in combination with methods and compositions set forth in US Pat. App. Docket No. OMNI-011 (097128-1036628 (021PV1), having the title "ALLELE-SPECIFIC CAPTURE OF NUCLEIC ACIDS", filed concurrently with the present application, and incorporated herein by reference. More specifically, one or more nucleic acids that are detected in a method set forth herein can be obtained using a polymerase-based method for selecting or capturing nucleic acids having target alleles of interest. Embodiments of the methods exploit the specificity with which a polymerase can form a stabilized ternary complex with a primed template and a next correct nucleotide. For example, a stabilized ternary complex can be formed between a polymerase, target allele and cognate nucleotide for the allele. An advantage of the methods is that polymerase specificity allows a target allele to be separated from other nucleic acids, including for example, other alleles that differ from the target allele by a single nucleotide. For example, a ternary complex can be formed between a polymerase, a primed template encoding a target single nucleotide polymorphism (SNP) allele and a cognate nucleotide for the SNP allele. Capture of the ternary complex will result in selective capture of the SNP allele, compared to a non-target SNP allele at the same locus, because the cognate nucleotide is selective for the target SNP when forming a ternary complex with the polymerase.

Methods and compositions set forth herein can be used to capture and optionally enrich rare alleles (e.g. DNA- or RNA-based) containing various mutations within their sequences. The methods are well suited to capture even rare variant alleles from pools of purified or semi-purified oligonucleotides containing wild-type DNA sequences of the same locus, as well as other unrelated sequences. The ternary complexes used for selective capture of target alleles can be configured as shown in FIG. 1A or FIG. 1B. The polymerase, nucleotide, primer or template that participates in ternary complex formation can be attached to a ligand that allows the ternary complex to be separated from other components of a sample. The ligand bearing ternary complex can be captured on a solid support having a receptor for the ligand. Optionally the solid support can be washed. The target allele can be detected on the solid support using methods set forth herein. Alternatively, the nucleic acid having the rare variant allele can be eluted by contacting the ternary complex with $Mg^{2+}$ or other ternary complex destabilizing conditions. The enriched allele can then be used in a detection method set forth herein.

Exemplary methods that can be used to enrich for target alleles include, for example, the following methods.

A method for separating a target allele from a mixture of nucleic can include steps of (a) providing a mixture of nucleic acids in fluidic contact with a stabilized ternary complex that is attached to a solid support, wherein the stabilized ternary complex includes a polymerase, primed nucleic acid template, and next correct nucleotide, wherein the template has a target allele, wherein the next correct nucleotide is a cognate nucleotide for the target allele, and wherein the stabilized ternary complex is attached to the solid support via a linkage between the polymerase and the solid support or via a linkage between the nucleotide and the solid support; and (b) separating the solid support from the mixture of nucleic acids, thereby separating the target allele from the mixture of nucleic acids.

In other embodiments, a method for separating a first allele of a locus from a second allele at the locus can include steps of (a) providing a mixture including the second allele in fluidic contact with a stabilized ternary complex that is attached to a solid support, wherein the stabilized ternary complex includes a polymerase, primer hybridized to a nucleic acid template, and next correct nucleotide, wherein the template has the first allele, wherein the next correct nucleotide is a cognate nucleotide for the first allele or the 3' end of the primer has a cognate nucleotide for the first allele, and wherein the stabilized ternary complex is attached to the solid support via a linkage between the polymerase and the solid support or via a linkage between the next correct nucleotide and the solid support; and (b) separating the solid support from the mixture of nucleic acids, thereby separating the first allele from the second allele.

In yet other embodiments, a method for separating first alleles at a plurality of loci from second alleles at the plurality of loci, respectively can be performed. The method can include steps of (a) providing a mixture of the second alleles at the plurality of loci, respectively, in fluidic contact with a plurality of stabilized ternary complexes that are solid support-attached, wherein the stabilized ternary complexes each include a polymerase, primed nucleic acid template, and next correct nucleotide, wherein the template includes a first allele, wherein the next correct nucleotide is a cognate nucleotide for the first allele or the 3' end of the primer includes a cognate nucleotide for the first allele, and wherein each of the stabilized ternary complexes is attached to the solid support via a linkage between the polymerase and the solid support or via a linkage between the next correct nucleotide and the solid support; and (b) separating the solid support from the mixture of nucleic acids, thereby separating the first alleles from the second alleles at the plurality of loci.

EXAMPLE I

Distinguishing the Next Correct Nucleotide from a Mismatched Nucleotide.

Methods & Materials. Polymerase buffer: 20 mM Tris, pH 8, 300 mM NaCl, 5 mM DTT, 100 µM dNTP, 150 nM Kienow, 0.01% BSA, 0.02% Tween-20, 10 mM $MgCl_2$. Exam buffer: 20 mM Tris, pH 8, 300 mM NaCl, 5 mM DTT, 100 µM dNTP, 150 nM Klenow, 0.01% BSA, 0.02% Tween-20. Incorporation buffer: 20 mM Tris, pH 8, 300 mM NaCl, 5 mM DTT, 0.01% BSA, 0.02% Tween-20, 10 mM $MgCl_2$. Wash Buffer: 20 mM Tris, pH 8, 300 mM NaCl, 5 mM DTT, 0.01% BSA, 0.02% Tween-20.

Figure 4:
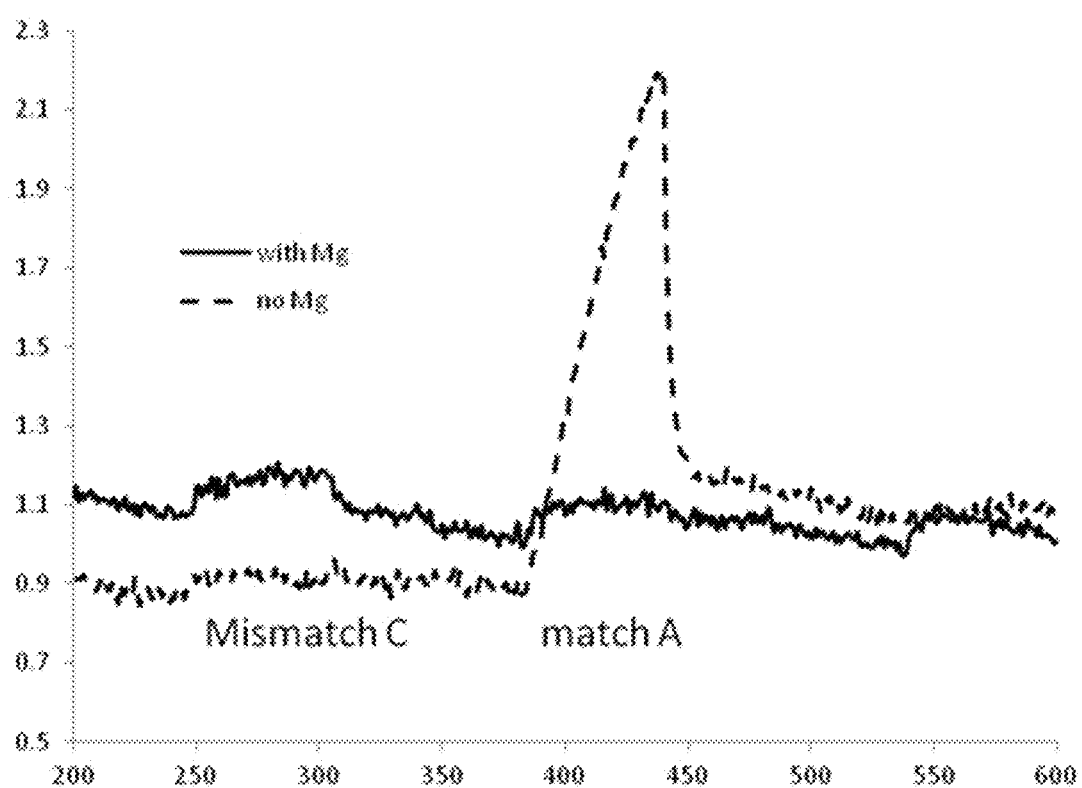
FIG. 4 is a graph showing the results of a binding assay using non-labeled optical detection methods where primed template, polymerase and nucleotide was incubated together in the presence or absence of magnesium.

FIG. 4 shows the results of a binding assay using polymerase, primed template, and nucleotide (either matched or mismatched with the next base in the template), where magnesium was present or absent during the binding assay. The first delivered nucleotide was dCTP (C:T mismatch) and the second delivery was dATP (A:T match). The solid line in FIG. 4 shows the results with Polymerase buffer. The pre-steady state rate constants were 0.0106 and 0.0084 for the match A and mismatch C steps, respectively. The difference was too small to accurately discriminate the cognate base. The dashed line in FIG. 1 represents a magnesium free binding step in Exam buffer, followed by soaking in incorporation buffer. A signal threshold of 1.1 nm allowed accurate identification of the correct base. These results show that the sensing platform was unable to discriminate a match from mismatch base when magnesium was included in the buffer during examination (Polymerase Buffer, solid line, FIG. 4). In contrast, binding in the absence of magnesium provided very large discrimination between correct and incorrect base (Exam Buffer, dashed line, FIG. 4). The correct base sequence was determined by signal thresholding rather than binding rates.

EXAMPLE II

Effect of Salt Concentration on Match/Mismatch Base Discrimination

The FORTEBIO® Octet instrument (Red384 or qk) (Menlo Park, Calif.) uses biolayer interferometry to measure binding reactions at the surface of a fiber optic tip. In this example, the tips were functionalized with streptavidin (SA) to enable binding to 5' biotin labeled DNA templates hybridized with a primer that is complementary to sequences near the 3' end of the template.

Experimental Conditions: PhiX_matchC and phiX_matchA were loaded onto individual tips. Primer-template was loaded onto the tips at between 100 and 500 nM in 1-2× PBS containing 0.01-0.02% BSA and 0.01-0.02% Tween 20 (loading buffer). The FP2 primer was in 1.25-2 fold excess over template. Loading was monitored by change in signal and usually reached a plateau within 5 minutes at 30 degrees C. Tips were soaked in Loading buffer for 1-5 minutes to remove unbound DNA material. For base calling, the tips were soaked in solutions containing IX Taq buffer (10 mM Tris-HCl, 50 mM KCl, pH 8.3, 25° C., magnesium free) supplemented with 0.01-0.02% BSA and 0.01-0.02% Tween 20 (LS buffer), 100 nM polymerase enzyme, 100 µM NTP, and varying concentrations of additional NaCl from 50 to 300 mM. The phiX_matchC duplex will form a ternary complex and show an increase in binding signal because the next correct nucleotide (cognate) is presented. The phiX_matchA should not because it is an incorrect nucleotide (noncognate).

Figure 5:
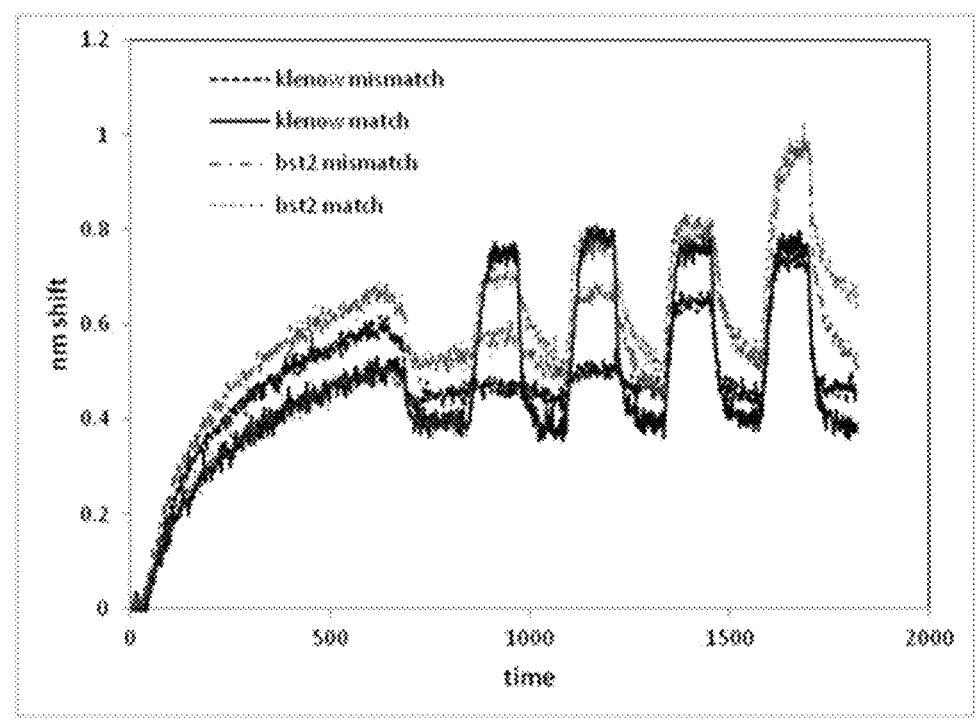
FIG. 5 is a graph showing the effects of salt concentration on match and mismatch base discrimination effects using biolayer interferometry on a FORTEBIO® Octet instrument (Menlo Park, Calif.).

Results: At standard reaction conditions both templates bound polymerase enzyme. However, as the salt concentration increased the binding affinity of the noncognate complex decreased while binding affinity of the cognate complex remained high. Thus, the signal to noise ratio (SNR) of base discrimination increased such that the next correct base was easily identified during this examination step (FIG. 5). Sodium chloride (NaCl) was used in this example but salts such as KCl, $NH_2(SO_4)$, potassium glutamate, and others known in the art can be used. Polymerases that show differences in binding affinity between correct and incorrect nucleotides included Klenow, Bst2.0, Bsu, and Taq.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. A method for identifying target alleles in a mixture of nucleic acids, comprising
   (a) providing an array of features, wherein different locus-specific primers are attached at different features of the array, wherein the different locus-specific primers comprise blocking groups that preclude enzymatic incorporation of an incoming nucleotide into the primer;
   (b) contacting the array with a plurality of nucleic acid templates, polymerases and nucleotides to form a plurality of stabilized ternary complexes at a plurality of the features,
   wherein the stabilized ternary complexes each comprises a polymerase, template nucleic acid comprising a target allele of a locus, a locus-specific primer of the array hybridized to the locus, and a next correct nucleotide that is a cognate to the target allele; and
   (c) detecting stabilized ternary complexes at the features, thereby identifying the target alleles.

2. The method of claim 1, wherein the blocking groups are reversible terminators.

3. The method of claim 1, wherein the blocking groups are irreversible terminators.

4. The method of claim 1, wherein the target allele occurs at a locus and the mixture of nucleic acids further comprises another allele at the locus.

5. The method of claim 1, wherein the nucleotides comprise exogenous labels, and wherein (c) comprises detecting stabilized ternary complexes at the features by detecting the exogenous labels, thereby identifying the target alleles.

6. The method of claim 5, wherein at least two types of nucleotides are contacted with the array in step (b), and wherein different exogenous labels distinguish at least two alleles at each locus in step (c).

7. The method of claim 1, further comprising
   (d) dissociating the next correct nucleotide from each feature of the array after the detecting of the stabilized ternary complexes, whereby the ternary complex at each of the features is converted to a binary complex comprising the polymerase, the template nucleic acid and the locus-specific primer from the ternary complex that was at the feature.

8. The method of claim 1, further comprising
   (d) dissociating the next correct nucleotide and the polymerase from each feature of the array after the detecting of the stabilized ternary complexes, whereby the ternary complex at each of the features is converted to a complex comprising the template nucleic acid and the locus-specific primer from the ternary complex that was at the feature.

9. The method of claim 8, further comprising washing the array after the dissociating.

10. The method of claim 8, further comprising
    (e) forming a second plurality of stabilized ternary complexes at a plurality of the features,
    wherein each of the features comprises the template nucleic acid and the locus-specific primer from the ternary complex that was at the feature, a polymerase and a next correct nucleotide that is a cognate to the target allele of the template nucleic acid.

11. The method of claim 10, further comprising
    (f) detecting stabilized ternary complexes of the second plurality at the features, thereby identifying the target alleles.

12. The method of claim 11, wherein a first type of nucleotide has a first type of exogenous label in step (c) and the first type of nucleotide has a second type of exogenous label in step (f).

13. The method of claim 12, wherein step (c) comprises detecting a first type of exogenous label on a first type of nucleotide, a second type of exogenous label on a second type of nucleotide, a third type of exogenous label on a third type of nucleotide and a fourth type of exogenous label on a fourth type of nucleotide.

14. The method of claim 13, wherein step (c) comprises detecting a first type of exogenous label on a first type of nucleotide, the first type of exogenous label on a second type of nucleotide, a second type of exogenous label on a third type of nucleotide and the second type of exogenous label on a fourth type of nucleotide.

15. The method of claim 14, wherein step (f) comprises detecting the second type of exogenous label on the first type of nucleotide, the second type of exogenous label on the second type of nucleotide, the first type of exogenous label on the third type of nucleotide and the first type of exogenous label on the fourth type of nucleotide.

16. The method of claim 1, wherein the polymerases comprise exogenous labels, and wherein (c) comprises detecting stabilized ternary complexes at the features by detecting the exogenous labels, thereby identifying the target alleles.

17. The method of claim 16, wherein a single type of nucleotide is contacted with the array in step (b).

18. The method of claim 1, wherein the ternary complex that is detected in step (c) lacks exogenous labels.

* * * * *